(12) United States Patent
Gilad et al.

(10) Patent No.: US 7,931,149 B2
(45) Date of Patent: Apr. 26, 2011

(54) SYSTEM FOR STORING AND ACTIVATING AN IN VIVO IMAGING CAPSULE

(75) Inventors: Zvika Gilad, Haifa (IL); Vitaly Roytenburd, Rishon Le'zion (IL)

(73) Assignee: Given Imaging Ltd., Yoqneam (IL)

( * ) Notice: Subject to any disclaimer, the term of this patent is extended or adjusted under 35 U.S.C. 154(b) by 0 days.

(21) Appl. No.: 12/473,064

(22) Filed: May 27, 2009

(65) Prior Publication Data
US 2010/0300922 A1 Dec. 2, 2010

(51) Int. Cl.
B65D 83/04 (2006.01)
B65D 85/42 (2006.01)

(52) U.S. Cl. .................. 206/530; 206/528; 206/477

(58) Field of Classification Search .................. 206/530, 206/528, 205, 210, 534, 539, 363, 438, 350, 206/818, 446, 439, 486, 488, 477, 478, 482, 206/480, 560; 600/109, 7, 114; 348/76, 348/77
See application file for complete search history.

(56) References Cited

U.S. PATENT DOCUMENTS

| | | |
|---|---|---|
| 3,683,389 A | 8/1972 | Hollis |
| 3,931,636 A | 1/1976 | Schneider |
| 3,971,362 A | 7/1976 | Pope et al. |
| 4,135,512 A | 1/1979 | Godsey |
| 4,172,640 A | 10/1979 | Land |
| 4,177,800 A | 12/1979 | Enger |
| 4,273,431 A | 6/1981 | Farmer et al. |
| 4,278,077 A | 7/1981 | Mizumoto |
| 4,411,257 A | 10/1983 | Machida |
| 4,646,724 A | 3/1987 | Sato et al. |
| 4,689,621 A | 8/1987 | Kleinberg |
| 4,741,327 A | 5/1988 | Yabe |
| 4,844,076 A | 7/1989 | Lesho et al. |
| 5,187,572 A | 2/1993 | Nakamura et al. |
| 5,257,636 A | 11/1993 | White |
| 5,267,033 A | 11/1993 | Hoshino |
| 5,279,607 A | 1/1994 | Schentag et al. |
| 5,365,267 A | 11/1994 | Edwards |
| 5,414,405 A | 5/1995 | Hogg et al. |
| 5,495,114 A | 2/1996 | Adair |
| 5,604,531 A | 2/1997 | Iddan et al. |

(Continued)

FOREIGN PATENT DOCUMENTS

DE 34 40 177 5/1986

(Continued)

OTHER PUBLICATIONS

U.S. Appl. No. 10/724,109, filed Dec. 1, 2003, Glukhovsky et al.

(Continued)

*Primary Examiner* — J. Gregory Pickett
*Assistant Examiner* — Ernesto A Grano
(74) *Attorney, Agent, or Firm* — Pearl Cohen Zedek Latzer, LLP (57) ABSTRACT

A storage unit is provided for removably storing an in vivo imaging capsule. The capsule may have a housing and an optical dome. The storage unit may include a recessed space formed for accepting the capsule. A magnet for magnetically activating and deactivating the capsule may be provided in the storage unit, for example in the lid. The storage unit may also include a capsule holding unit comprising at least two protruding elements to removably hold the capsule in the storage unit, wherein the protruding elements are positioned to grip the capsule housing.

18 Claims, 7 Drawing Sheets

U.S. PATENT DOCUMENTS

| | | | |
|---|---|---|---|
| 5,783,389 A | 7/1998 | Vo-Dinh | |
| 5,819,736 A | 10/1998 | Avny et al. | |
| 5,820,547 A | 10/1998 | Strobl et al. | |
| 5,833,603 A | 11/1998 | Kovacs et al. | |
| 5,886,353 A | 3/1999 | Spivey et al. | |
| 5,909,026 A | 6/1999 | Zhou et al. | |
| 5,929,901 A | 7/1999 | Adair et al. | |
| 5,967,979 A | 10/1999 | Taylor et al. | |
| 5,986,693 A | 11/1999 | Adair et al. | |
| 5,993,378 A | 11/1999 | Lemelson | |
| 6,043,839 A | 3/2000 | Adair et al. | |
| 6,106,457 A | 8/2000 | Perkins et al. | |
| 6,117,529 A | 9/2000 | Leising et al. | |
| 6,240,312 B1 | 5/2001 | Alfano et al. | |
| 6,371,927 B1 | 4/2002 | Brune et al. | |
| 6,393,431 B1 | 5/2002 | Salvati et al. | |
| 6,594,036 B1 | 7/2003 | Wong et al. | |
| 6,764,440 B2 | 7/2004 | Iddan et al. | |
| 6,934,573 B1 | 8/2005 | Glukhovsky et al. | |
| 7,295,226 B1* | 11/2007 | Meron et al. | 348/77 |
| 2001/0035902 A1 | 11/2001 | Iddan et al. | |
| 2002/0103417 A1 | 8/2002 | Gazdzinski | |
| 2003/0028078 A1 | 2/2003 | Glukhovsky | |
| 2004/0254455 A1* | 12/2004 | Iddan | 600/424 |
| 2005/0159646 A1 | 7/2005 | Nordstrom et al. | |
| 2007/0055177 A1* | 3/2007 | Fukuda et al. | 600/593 |
| 2008/0027267 A1* | 1/2008 | Segawa | 600/7 |
| 2008/0033243 A1 | 2/2008 | Adler et al. | |
| 2008/0039675 A1* | 2/2008 | Segawa | 600/7 |
| 2008/0060952 A1* | 3/2008 | Negron | 206/205 |
| 2009/0118581 A1 | 5/2009 | Meron et al. | |

FOREIGN PATENT DOCUMENTS

| | | |
|---|---|---|
| EP | 0 969 083 | 1/2000 |
| JP | 53-66192 | 3/1978 |
| JP | 53-66192 | 6/1978 |
| JP | 5745833 | 3/1982 |
| JP | 3289779 | 12/1991 |
| JP | 4109927 | 4/1992 |
| JP | 1992-144533 | 5/1992 |
| JP | 4180736 | 6/1992 |
| JP | 5015515 | 1/1993 |
| JP | 5-76483 | 3/1993 |
| JP | 05-76483 | 3/1993 |
| JP | 5-137693 | 6/1993 |
| JP | 5137693 | 6/1993 |
| JP | 06-43989 | 2/1994 |
| JP | 6-43989 | 6/1994 |
| JP | 6285044 | 10/1994 |
| JP | 07-184837 | 7/1995 |
| JP | 7-184837 | 7/1995 |
| JP | 7184837 | 7/1995 |
| JP | 8-110479 | 4/1996 |
| JP | 8110479 | 4/1996 |
| JP | 9-327447 | 12/1997 |
| JP | 10-165027 | 6/1998 |
| JP | 10165027 | 6/1998 |
| JP | 2001-224553 | 8/2001 |
| JP | 2005-003829 | 1/2005 |
| JP | 3114299 | 10/2005 |
| JP | 3753730 | 10/2005 |
| WO | WO 91/06855 | 5/1991 |
| WO | WO 92/21307 | 12/1992 |
| WO | WO 98/11816 | 3/1998 |
| WO | WO 98/52042 | 11/1998 |
| WO | WO 00/22975 | 4/2000 |
| WO | WO 00/76391 | 12/2000 |
| WO | WO 01/08548 | 2/2001 |
| WO | WO 01/35813 | 5/2001 |
| WO | WO 01/50941 | 7/2001 |
| WO | WO 02/080376 | 10/2002 |
| WO | WO 02/094337 | 11/2002 |
| WO | WO 02/095351 | 11/2002 |
| WO | WO 03/003706 | 1/2003 |
| WO | WO 03/011103 | 2/2003 |
| WO | WO 03/028224 | 4/2003 |
| WO | WO2007/126247 | 11/2007 |

OTHER PUBLICATIONS

Office Action of U.S. Appl. No. 10/130,326, dated Nov. 4, 2005.
Office Action for U.S. Appl. No. 10/130,326, dated Aug. 11, 2006.
Office Action of U.S. Appl. No. 09/800,470, dated Aug. 4, 2005.
Office Action of U.S. Appl. No. 09/800,470, dated Sep. 27, 2004.
Notice of Allowance of U.S. Appl. No. 10/130,326, dated Aug. 7, 2007.
BBC News Online—Pill camera to 'broadcast from the gut', Feb. 21, 2000, www.news.bbc.co.uk.
Manual of Photogrammetry, Thompson (Ed.), Third Edition, vol. Two, American Society of Photogrammetry, 1966.
The Radio Pill, Rowlands, et al., British Communications and Electronics, Aug. 1960, pp. 598-601.
Video Camera to "TAKE"—RF System lab.
Wellesley company sends body montiors into space—Crum, Apr. 1998.
Wireless transmission of a color television moving image from the stomach using a miniature CCD camera, light source and microwave transmitter. Swain CP, Gong F, Mills TN. Gastrointest Endosc 1997;45:AB40.
www.jason.net—Tiny cam © 2000.
www.pedinc.com—Personal Electronic Devices, Inc. © 1997.
"John Hopkins Device Takes John Glenn's Temperature in Space", The John Hopkins University Applied Physics Laboratory, Nov. 4, 1998, www.jhuapl.edu/newscenter/pressreleases/1998/glenn.htm.
"PED uses PICMicro® Device to Monitor John Glenn During Space Shuttle Mission", www.microchip.com, retrieved Sep. 8, 2005.
Notice of Allowance, issued Mar. 31, 2010, for U.S. Appl. No. 11/905,677.
Notice of Allowance, issued Sep. 16, 2010, U.S. Appl. No. 12/351,133.
U.S. Appl. No. 10/046,541, filed Jan. 16, 2002, Meron.
Translated Office Action of Application No. 2001-537812 dated Apr. 18, 2008.

* cited by examiner

SYSTEM FOR STORING AND ACTIVATING AN IN VIVO IMAGING CAPSULE

FIELD OF INVENTION

The present invention relates to an in-vivo device and method such as for imaging an in-vivo lumen. More specifically, the present invention relates to a method and apparatus for storing and activating an in-vivo imaging capsule.

BACKGROUND OF THE INVENTION

Known devices may be helpful in in-vivo sensing, such as imaging or pH sensing. Autonomous in-vivo sensing devices, such as swallowable or ingestible capsules or other devices, may move through a body lumen, sensing as they move along. An autonomous in-vivo sensing device such as an imaging device may include, for example, an imager for obtaining images from inside a body cavity or lumen, such as the gastrointestinal (GI) tract while the in-vivo imaging device passes through the GI lumen. The imager may, for example, be associated with an optical system, and optionally a transceiver and an antenna. Some of these devices use a wireless connection to transmit image data. Other devices, systems and methods for in-vivo sensing of passages or cavities within a body, and for sensing and gathering information (e.g., image information, pH information, temperature information, electrical impedance information, pressure information, etc.), are known in the art.

A user who is swallowing an imaging capsule may not be aware of the need to activate the capsule in order to start the imaging procedure. In some cases, it is not possible to retrieve or to activate the capsule after it has been swallowed. Therefore there is a need for a swallowable capsule to be easily and automatically activated before it is swallowed, to prevent involuntary or unintentional swallowing of a deactivated capsule. However, an imaging capsule should not be activated accidentally or involuntarily, for example during shipping and handling of the capsule in its package, since such activation may deplete the capsule's battery and cause the imaging procedure to fail. In some cases, a user or doctor may want to test whether the capsule is working, and may wish to deactivate it immediately. It may be useful to provide a storage unit that enables easy activation and deactivation of the imaging capsule.

Known packaging solutions exist for storing an in vivo imaging capsule. These solutions may include devices and methods for activating in vivo imaging capsules, for example as disclosed in U.S. Pat. No. 7,295,226 to Meron et al which is hereby incorporated by reference. For example, Meron discloses in col. 2 line 59-col. 3 line 20 an external magnet which may impose inhibition of a power source of a component essential to the image collecting process. The external magnet may be part of or attached to the medical device package and is removed once the device package is removed. In col. 4 lines 24-41, Meron discloses that once the capsule is released from its package and it is distanced from magnet, and the imaging device and/or other components essential for the imaging collecting process in capsule are activated and the imaging system begins capturing images.

The optical dome covering the capsule's optical system may be made of a transparent material, in order to enable high quality imaging of, for example, the gastrointestinal tract. Maintaining high quality imaging may enable better diagnosis by the specialist reviewing the images. The optical dome may be sensitive to scratches or deformation, which may occur during transportation, shipping and/or handling of the capsule in its package. Deformation or dirt may obscure the imaging field of view, and/or may cause imaging artifacts which reduce the quality of the images captured by the imaging capsule. The optical dome may also be sensitive to dirt, grease and/or fingerprints, which may be transferred onto the optical dome when a patient touches the capsule, for example during the swallowing procedure. Images with artifacts or with a reduced field of view may reduce the detectability of pathologies or abnormalities by the specialist reviewing the image stream. The size of the optical dome may vary, for example a larger dome may be used to enlarge the capsule's imaging field of view. A large dome may be more prone to damaging or accidental scratching, breaking or impairment. When extracting a capsule with a large optical dome or a capsule with more than one optical dome from its storage unit, it is preferable to reduce touching of the optical dome, in order to prevent damaging or soiling it. Therefore it may be advantageous to provide a storage device which securely holds an imaging capsule for shipping, and which allows retrieving a capsule with a large optical dome or a double-headed capsule without touching its optical domes.

Storing devices for example such as disclosed in U.S. Pat. No. 7,295,226 to Meron et al may be primarily designed, for example, for holding and protecting an imaging capsule with a single optical head, and may be less desirable for an imaging capsule with more than one optical head. Meron et al. disclose a swallowable imaging capsule inserted into a cup such that a portion of the swallowable imaging capsule is held by the cup and a portion of the swallowable imaging capsule protrudes from the cup. However, the act of removing an imaging capsule with for example two optical domes located at opposite ends of the capsule from such a storage device may cause the user to touch one of the optical domes which is not inserted into the cup. The same dome may also be damaged during the shipping of the capsule in its package.

Therefore there is a need for a storing device which can safely protect an imaging capsule with more than one optical head and allow easy activation and extraction of the capsule from the storing device.

SUMMARY OF THE INVENTION

According to one embodiment of the present invention, storage unit may be provided for removably storing an in vivo imaging capsule. The in vivo capsule may be a swallowable capsule, and may have a housing and an optical dome. In one embodiment, the storage unit may include: a recessed space formed for accepting the capsule, a magnet for magnetically activating and deactivating the capsule, and a capsule holding unit. The capsule holding unit may comprise at least two protruding elements which may removably hold the capsule in the storage unit. The protruding elements may be positioned to grip the capsule substantially around its housing. In one example, the capsule holding unit may be positioned substantially within the recessed space. According to one embodiment, the storage unit may comprise a lid, and the magnet may be positioned on the lid. The magnet may activate the capsule when the lid is open, and may deactivate the capsule when the lid is closed.

In one embodiment, one or more fastening elements may be positioned on the lid. When the lid is in closed position, the protruding elements may be pressed towards the stored capsule, for example by the fastening elements. The protruding elements may be positioned symmetrically across from each other, for example on opposite sides of the recessed space of the storage unit.

In one embodiment, the storage unit may include a magnet for magnetically activating and deactivating the capsule. The magnet may be embedded into a fastening element which may be, for example, connected to the lid. The magnet may also be glued, welded or otherwise connected into the lid itself. In one embodiment, the lid or for example a portion of the lid may be made of a transparent material.

In one embodiment, the capsule holding unit may comprise one or more capsule gripping units. Each capsule gripping unit may comprise two protruding elements, positioned for example substantially symmetrically across from each other on opposite sides of the recessed space of the storage unit. The capsule gripping units may be positioned substantially one centimeter apart from each other. In other embodiments, the capsule gripping units may be positioned differently, for example closed together or further apart.

A storage device is provided according to one embodiment for storing a swallowable capsule. The storage device may comprise, in one embodiment, a container base with a recessed space for placing the swallowable capsule, a capsule holding unit which may be positioned for example substantially within in the container base, and a lid for covering the container base. The lid may comprise a magnet, which may be positioned to activate the swallowable capsule when the lid is open, and to deactivate the swallowable capsule when the lid is closed. The capsule holding unit may comprise for example two protruding elements, which may be positioned to removably hold the swallowable capsule around its housing. The lid may comprise a fastening element to press on the two protruding elements when the lid is closed, causing the swallowable capsule to be held in the capsule holding unit. The storage device may further comprise a liner, which may be assembled into the container base.

In one embodiment, the magnet may be embedded into the lid or into the fastening element. The lid may include a transparent portion, made of a transparent material.

In one embodiment, a method may be provided for packaging a swallowable capsule. A container base may be provided, for example the base may include a connecting element. A capsule holding unit with protruding elements may be connected to the container base connecting element. The method may include the step of assembling a liner onto the container base. In one embodiment the liner may be provided with one or more fissures for the protruding elements. A lid comprising a magnetic element for activating the swallowable capsule may be attached to the container base, and a fastening element which may be provided for example on the lid may press the protruding elements together.

The swallowable capsule may be inserted into the capsule holding unit, which may hold the capsule around the capsule housing. The lid may be closed in order to apply pressure to the protruding elements of the capsule holding unit, and to deactivate the capsule. In some embodiments, the swallowable capsule may be rotated around its axis to deactivate it.

According to one embodiment, a method of storing and activating an in vivo imaging capsule may comprise activating an illumination source of the swallowable capsule to indicate whether the swallowable capsule is activated.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention.

Some embodiments of the present invention are directed to storing and activating an in-vivo device that may be inserted (e.g., by swallowing) into a body lumen, e.g., the gastro-intestinal (GI) tract, for example, from outside the body. Some embodiments are directed to a typically one time use or partially single use detection and/or analysis device. Some embodiments are directed to storing a typically swallowable in-vivo device that may passively or actively progress through a body lumen, e.g., the gastro-intestinal (GI) tract, for example, pushed along by natural peristalsis. Some embodiments are directed to storing in-vivo sensing devices that may be passed through other body lumens, for example, through blood vessels, the reproductive tract, or the like. The in-vivo device which may be used in conjunction with embodiments of the present invention may be, for example, a sensing device, an imaging device, a diagnostic device, a detection device, an analysis device, a therapeutic device, or a combination thereof. In a preferred embodiment, the in-vivo device may include an image sensor or an imager and/or other suitable components. Some embodiments of the present invention may be directed to other imaging devices, not necessarily in-vivo imaging.

Devices, systems and methods which may be used in conjunction with some embodiments of the present invention, including for example in-vivo sensing devices, may be similar to embodiments described in U.S. application Ser. No.

10/046,541 to Meron et al., entitled "System and method for wide field imaging of body lumens", which is hereby incorporated by reference in its entirety. For example, an imaging capsule with two optical systems located in each end of the capsule as shown in FIG. 4 of the application may be used in conjunction with embodiments of the present invention. A normally-closed magnetic MEMS switch as described for example in FIGS. 2A and 2B of US Patent Application Publication Number 2004/0254455 to Iddan et al. which is hereby incorporated by reference, may be incorporated into imaging capsules which may be used with a device, system and method according to an embodiment of the present invention.

Embodiments of the in-vivo device are typically autonomous and are typically self-contained. For example, the in-vivo device may be or may include a capsule or other unit where all the components are substantially contained within a container, housing or shell having one or more optical dome(s) to complete an enclosed package, and where the in-vivo device does not require any wires or cables to, for example, receive power or transmit information. The in-vivo device may communicate with an external receiving and display system to provide display of data, control, or other functions. For example, power may be provided by an internal battery or an internal power source, or using a wired or wireless power-receiving system. Other embodiments may have other configurations and capabilities. For example, components may be distributed over multiple sites or units; and control information or other information may be received from an external source.

Figure 1:
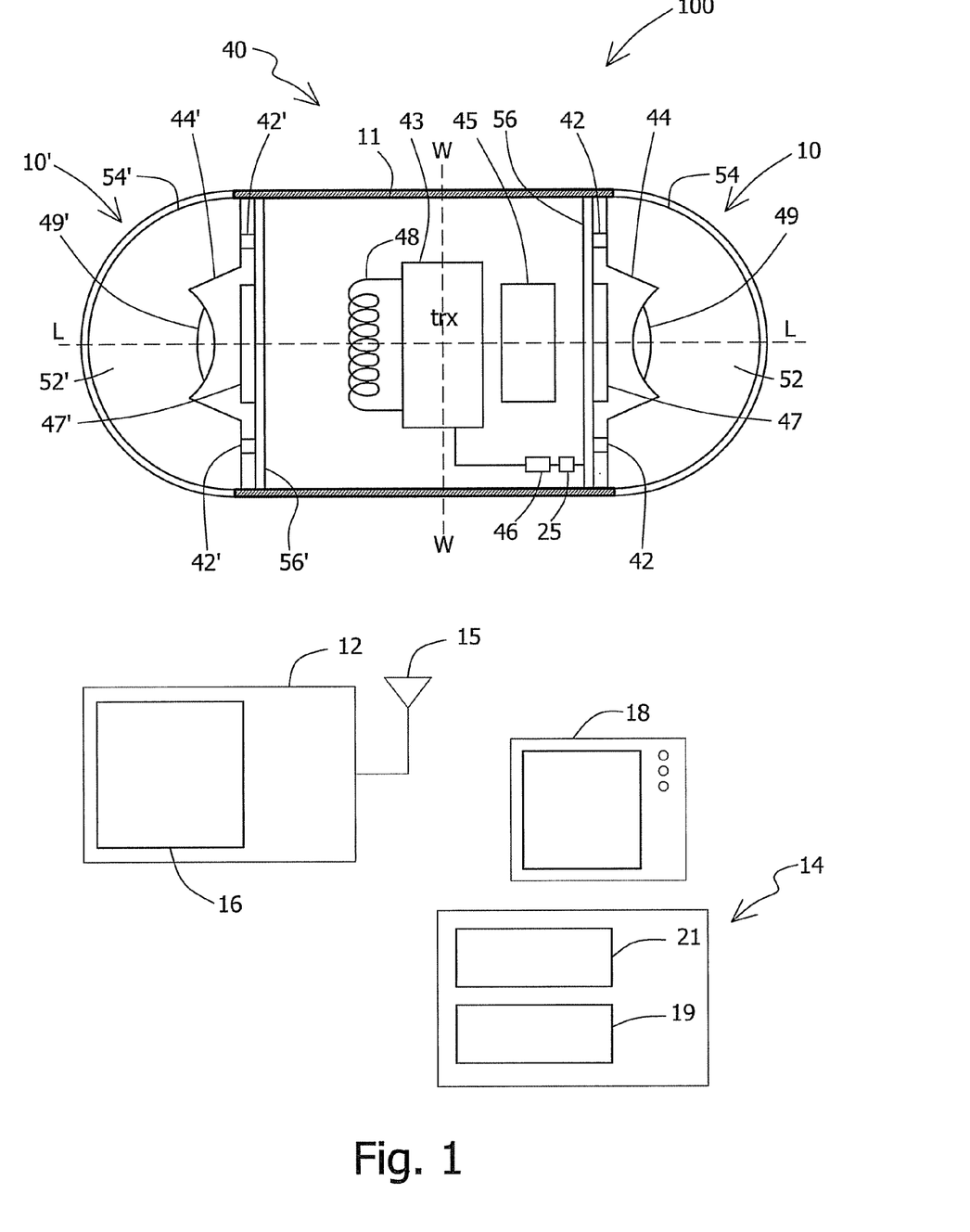
FIG. 1 is a schematic illustration of an in-vivo system according to an embodiment of the invention.

Reference is made to FIG. 1, which schematically illustrates an in-vivo system 100 in accordance with some embodiments of the present invention. One or more components of the system may be used in conjunction with, or may be operatively associated with, the devices and/or components described herein or other in-vivo devices in accordance with embodiments of the invention.

The in-vivo imaging system 100 may include, for example an in-vivo imaging capsule 40. The in-vivo capsule 40 may be, for example, a swallowable capsule capturing images and possibly other data. The in-vivo capsule 40 may be in the shape of a capsule, including for example one or more viewing windows or domes 54 (and/or 54'); other shapes may be used, and the device need not be swallowable or a capsule. The capsule 40 may be capsule shaped, or may have other shapes, for example, an elongated capsule, a peanut shape, tubular, conical, cylindrical, or other suitable shapes. The size of the capsule 40 may be dictated by various factors, such as a size which may comfortably be swallowed by a person, whether an adult or child. The size of the main components required in capsule 40 may also affect the size of the capsule, for example, the size of one or more batteries 45, the distance of the focus of the optical system 10, and the number and size of lenses 49 and 49' in the optical system 10. The material of optical domes 54 and 54' may cause the domes to be sensitive to scratches, breakage and/or soiling. For example, if the capsule 40 contacts the walls of the storage box, the optical domes may become scratched or damaged, thus causing image artifacts or poor quality of images. In some cases, the user's fingers may touch the optical domes 54 and 54', and may soil one or more of the optical domes 54 and 54'. In some embodiments, the capsule 40 may be manufactured and stored in sterile or substantially clean conditions, and the patient may remove the capsule 40 from the storage box, so that the medical professional does not touch it before the patient swallows the capsule 40. The size of capsule 40 also may affect the ability to hold without contacting the optical domes 54 and 54' or with minimum contact of the fingers with the optical domes 54 and 54'. It may be beneficial to grab the capsule 40 by holding it substantially around the housing 11, for example by grabbing it around its longitudinal axis L between a forefinger and a thumb.

Capsule 40 may include one or more imaging heads. An imaging head may include, for example, an optical system 10 and one or more illumination sources 42. Other components may be included in the imaging head, such as processing circuits or chips, one or more substrates on which the illumination sources may be assembled or connected, a viewing window or dome 54 that may cover the optical system, etc. Capsule 40 may include one or more optical systems 10 (and/or 10') including, for example, one or more lens(es) 49 and 49', lens holders, baffles, or separators 44 (and/or 44'), one or more sensors such as imagers 47 (and/or 47'), for capturing images, and one or more processing chips or circuits that process the signals generated by the one or more imagers 47 (and/or 47'). A processing circuit need not be a separate component; for example, processor or a processing chip may be integral to the imager 47. The processing circuit may be divided into several different units or separate components. One or more illumination source(s) 42 (and/or 42'), for example a set of light emitting diodes (LEDs), organic LEDs (OLEDs), or other suitable light sources, may provide light to illuminate objects. A double-headed imaging capsule as shown in FIG. 1 may include two substantially identical optical systems. In other embodiments, the capsule may include more than two optical systems, which may not be substantially identical (for example, one optical system may have a wide field of view while the other may have a narrower field of view). In addition, a device with only one optical dome and optical system may be used.

According to one embodiment of the present invention, the capsule 40 may include a transmitter/receiver 43 such as an ASIC, for transmitting and/or receiving image and other (e.g., non-image) information to a receiving device, and may include other components. The transmitter/receiver 43 may be an ultra low power radio frequency (RF) transmitter with high bandwidth input, possibly provided in chip scale packaging, and may be combined with processing chip or circuit. The transmitter/receiver 43 may transmit and/or receive via for example an antenna 48. Other methods of transmission may be used. The transmitter/receiver 43 may also act as a controller and include circuitry and functionality for controlling the capsule 40, although a separate control unit may be used. The device may include a power source 45, such as one or more batteries. For example, the power source 45 may include silver oxide batteries, lithium batteries, or other electrochemical cells having a high energy density, or the like. Other power sources may be used.

Other components and sets of components may be used. For example, the power source may be capable of receiving power from an external power source transmitting power to the capsule 40, and a controller separate from the transmitter/receiver 43 may be used.

In one embodiment, the imager 47 may be a complementary metal oxide semiconductor (CMOS) imaging camera. The CMOS imager is typically an ultra low power imager and is provided in chip scale packaging (CSP). Other types of CMOS imagers may be used. In another embodiment, another imager may be used, such as a CCD imager, or another imager. According to other embodiments a 320×320 pixel imager may be used. Pixel size may be between 5 to 6 microns. According to some embodiments pixels may be each fitted with a micro lens. Other dimensions for imagers and other numbers of pixels may be used.

Imager 47 may be fixed or otherwise attached to a substrate such as, for example, substrate or circuit board 56. In other embodiments, circuit board 64 may be further attached to a substrate 56, which may for example support illumination source(s) 42 (which may be supported by its/their own substrate or circuit board, which may be supported by or integrated with substrate 56) and which may define a viewing axis L of capsule 40. Substrate 56 may be for example a rigid circuit board, a partially-rigid and partially-flexible or a completely flexible circuit board. In other embodiments, illumination source(s) may be positioned on a different plane than, for example, imager 47. A capsule housing 11 may encase the capsule 40 when in combination with optical dome(s) 54 (and possibly 54'). The housing 11 may have a substantially cylindrical shape, with the one or more optical domes 54 (and/or 54') connected to the housing to form for example a capsule shape and enclose the components.

In some embodiments an activation controller 46 may be provided in the capsule and may be programmable before or after swallowing the capsule. Activation controller 46 may be a separate component, or may be integrated into, for example, an ASIC as part of transmitter 43, reception unit 12, imager 47 (and/or 47') or any other component in in-vivo imaging capsule 40 or in the extra body unit. In some embodiments activation controller 46 may include a switch (such as a MEMS switch or a reed switch RI-80 SMD), for example a magnetic switch 25 as shown in FIG. 1, although the switch may be separate or may be part of a different component of capsule 40. As described in FIGS. 2A and 2B of US Patent Application Publication Number 2004/0254455 to Iddan et al., switch 25 may include several layers or terminals. A first terminal may be made of non-magnetic conductive material, such as non-magnetic metal, for example, gold or chromium or any other suitable, conductive material or alloy. A second and third terminal may be made, for example, of a typically soft, ferromagnetic, conductive material, for example, Permalloy, and may be coated with a suitable non-stiction layer, which may prevent these terminals from resisting separation after being in contact. One of the terminals may be a flexible ferromagnetic conductive terminal when placed in the proximity of a magnetic field. Upon placement of switch 25 in proximity to magnets such as magnets 620 and 621 (FIG. 2), switch 25 may for example open. For example the second and third terminals attain magnetic properties and the second terminal may bend or move away from the first terminal, creating an open position between the first and the second terminals. In other embodiments, a conductive layer may bend and touch another conductive layer, forming and/or closing an electric circuit and creating a closed position between the two conductive layers, and as a result cause the switch to be in an open mode. According to some embodiments, when the switch 25 is placed in proximity to one or more external magnets, for example magnets 620 and 621, switch 25 is switched to an open mode. It is noted that magnets 620 and or 621 may include any suitable magnet or source of magnetic field, for example, a ballast magnet, a permanent magnet, an electromagnetic coil, and the like. In some embodiments, for example when switch 25 is switched to an open mode, the illumination source(s) 42 (and/or 42') may be activated, for example, simultaneously, with the imager 47, thereby obtaining an image of the illuminated body lumen area. In some embodiments, the one or more illumination source(s) 42 and/or 42' may be activated in an alternating manner such as blinking, or selectively activated. In other embodiments, the capsule 40 may comprise a different type of switch, e.g. a temperature switch or an RF switch. In yet another embodiment, the activation of the in-vivo device may be achieved with an external power source (not shown) as disclosed in International PCT Application Publication Number WO 2007/126247 to Shim et al. In other embodiments, a magnetic field may hold a switch closed.

Preferably, located outside the patient's body in one or more locations, external to the in-vivo capsule 40, are a receiver 12, preferably including an antenna or antenna array 15, for receiving image and possibly other data from capsule 40, and a receiver storage unit 16, for storing image and other data received by the receiver 12. Additional components located externally to the patient may include a data processor 14 which may comprise a data processor storage unit 19, and an image monitor 18, for displaying, inter alia, the images transmitted by the capsule 40 and recorded by the receiver 12. Typically, the receiver 12 and receiver storage unit 16 are small and portable, and are worn on the patient's body during recording of the images. Preferably, data processor 14, data processor storage unit 19 and monitor 18 are part of a personal computer or workstation, which may include components such as a processor or controller 21, a memory (e.g., storage 19, or other memory), a disk drive, and input-output devices, although alternate configurations are possible. In alternate embodiments, the data reception and storage components may be of another configuration. A data decompression module for decompressing data received from receiver 12 or from the capsule 40 may also be included in the personal computer or workstation.

Figure 2:
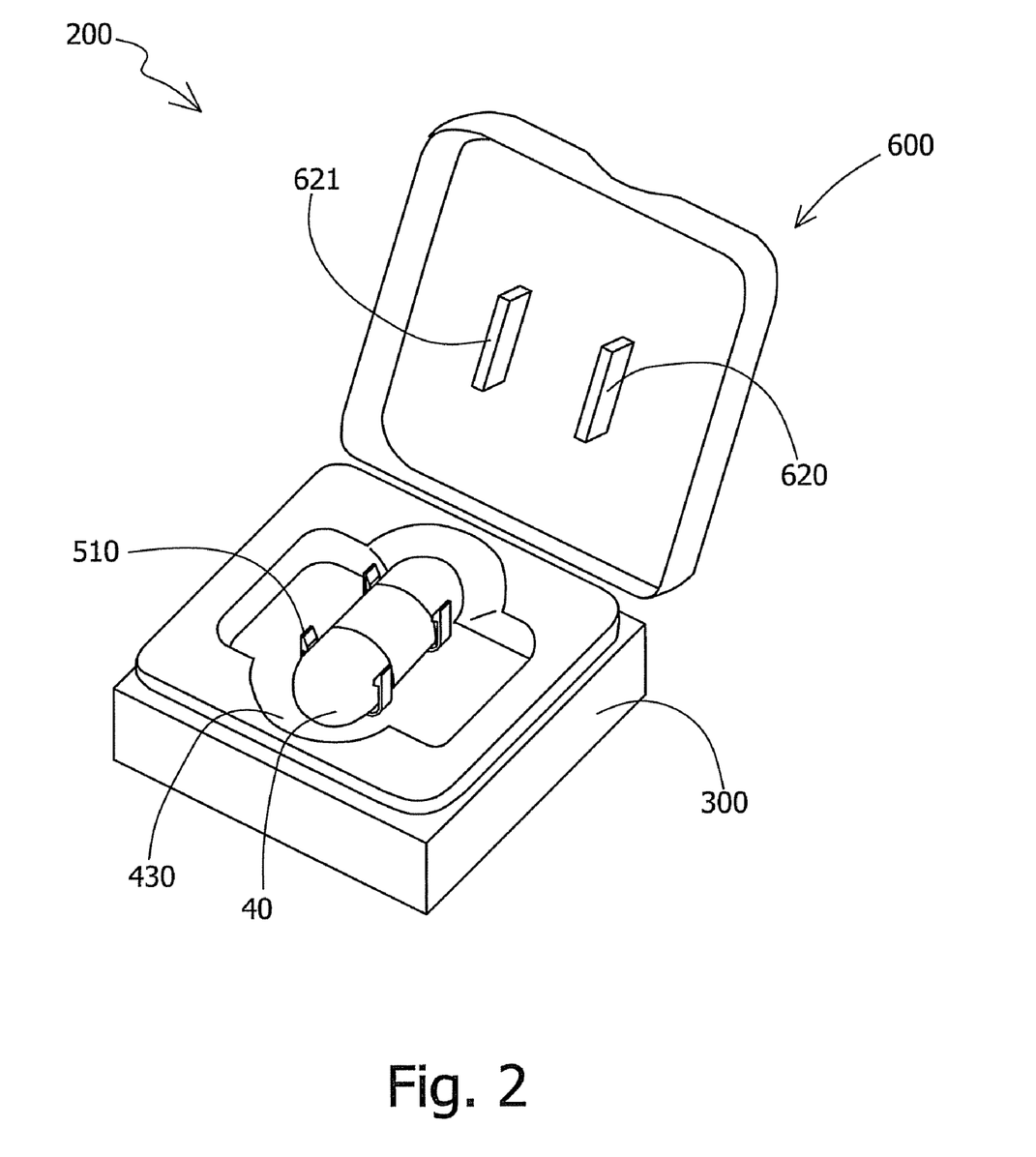
FIG. 2 is a schematic illustration of a device for storing and activating an in vivo imaging capsule according to an embodiment of the invention.

Reference is now made to FIG. 2, which is a schematic illustration of a device for storing and activating an in vivo imaging capsule according to an embodiment of the invention. The storing unit 200 may hold a swallowable capsule 40 and protect it during transport or handling, such that even if the package holding one or more capsules is dropped or mishandled, the capsules may remain whole, unharmed and intact. The storing unit 200 may comprise, for example, a container base 300 which may be the bottom part of an outer shell of the device. The container base 300 is preferably made of a plastic or rubber material such as Santoprene™ thermoplastic elastomer, polycarbonate or acrylonitrile butadiene styrene (ABS), or from a carton or paper material, or a combination of plastic and carton. The container base 300 may be of a size appropriate for holding an imaging capsule 40. The storing unit 200 may include a liner 400 which may be positioned on top of the container base 300. The liner 400 may include a concave or recessed space 430 for placing an imaging capsule 40, or which may accept capsule 40. In other embodiments, the portion forming the recessed space 430 need not be on a liner, and may be for example integral with the base 300. The recessed space 430 may be shaped substantially spherically, or as an oval, as an egg or as a rectangle with round corners, in such a manner as to allow an imaging capsule 40 or another object shaped for example as a sphere or an elongated sphere, an egg, or a cylindrical object having rounded or domed ends, to lie inside the recessed space 430. The recessed space 430 may have other shapes, for example the recessed space 430 may include additional recessed portions located adjacent to the oval recessed portion such as portions 412 and 413 in FIG. 4, which may be shaped like cylinders, squares, circles, or substantially as rectangles with rounded corners, and may allow a user's fingers to easily pick up the capsule 40 and remove it from the liner 400. Liner 400 may be made of a soft or a hard material (such as a plastic or rubber materials for example Santoprene™ thermoplastic elastomer, polycarbonate or ABS, or from a carton or paper or cardboard material, or a combination of plastic and paper or cardboard.). Liner 400 may have a certain rigidity or hardness, for example of 70-90 Shore. Liner 400 may be removably connected to container base 300, and may be removably connected to a capsule holding unit 260 which may be positioned in the concaved space 430 of liner 400. The capsule holding unit 260 is shown and described in detail in FIG. 5. While in some embodiments different components such as the base, holding unit and liner are separate units, in alternate embodiments one or more of these units may be integral with each other. Other dimensions and specifications (e.g., Shore) may be used.

In some embodiments of the present invention, lid 600 may be connected to the container base 300, for example by one or more hinges, pins, screws, or by one or more adhesive and/or sticker elements (not shown) that may be connected (glued for example) to lid 600 and to container base 300 thereby acting as a pivot for opening and closing the lid 600. The lid 600 may include one or more magnetic elements 620 and 621, which when introduced near or distanced from the capsule 40 may magnetically activate or deactivate the capsule 40 respectively. In some embodiments, the magnetic elements 621 and 620 may be ring shaped or curved so that no specific directionality or orientation (for example, a specific angle) of the capsule 40, in relation to the magnets, is required. In some embodiments, opening the lid 600 may distance the magnetic elements 620 and 621 from the capsule 40 thus activate the capsule 40. Magnetic elements 620 and 621 may be embedded or glued into slots or clefts in lid 600, or may be inserted for example into fastening elements 630 and 631 as described in FIG. 6A. Upon the activation of the capsule 40, one or more illumination source(s) 42 and/or 42' of capsule 40 may start illuminating or blinking, and an image capturing procedure may be initiated. Closing the lid 600 may move the magnetic elements near the capsule 40 thus deactivating the capsule 40. Upon the deactivation of the capsule 40 the one or more illumination source(s) 42 and/or 42' of capsule 40 may stop illuminating or blinking. Lid 600 may be made of a transparent or translucent material, partially or completely, and the illuminated illumination source(s) 42 and/or 42' of the capsule 40 may be seen through the transparent or translucent section (e.g., a window), thereby enabling a user to verify if the capsule 40 is activated while the lid 600 is shut. Preferably, the capsule 40 is deactivated while positioned in the storing unit 200 when the lid 600 is in closed position for example a completely closed position as shown in FIG. 7C, or a partially closed position. The capsule 40 may be activated when the lid 600 is in a partially open position (for example as shown in FIG. 2) or in a completely open position. It may be possible to verify if the capsule 40 is working properly by opening lid 600 and closing it, by seeing if the illumination source(s) 42 and/or 42' start illuminating when the lid 600 is opened and stop illuminating when the lid 600 is closed.

Figure 3:
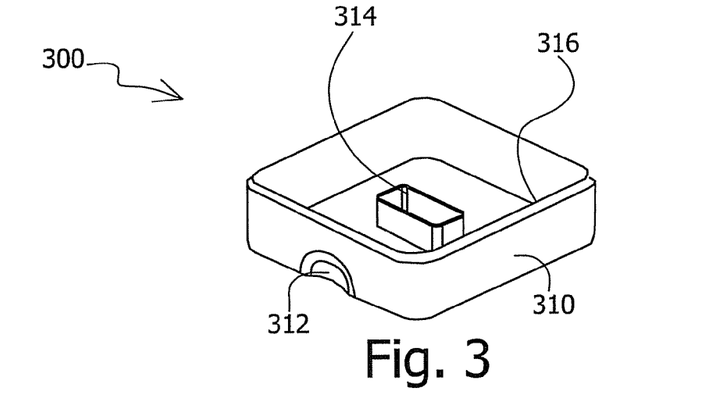
FIG. 3 is a schematic illustration of a container base of a device for storing and activating an in vivo imaging capsule according to an embodiment of the invention.

Reference is now made to FIG. 3, which is a schematic illustration of a container base of a device for storing and activating an in vivo imaging capsule 40 according to an embodiment of the invention. The container base 300 may be shaped substantially like a box, but may also be circular, oval, or any other suitable shape. The outer shell 310 may be indented partially or substantially around the top 316 to allow a lid 600 to close tightly over the container base 300. One or more indent(s) or concave segment(s) 312 may be positioned near the lower part of the outer shell 310, and may used for placing a finger or a thumb while opening and/or closing the storing unit 200. The concave section 312 may be covered by or made with a material that enables a firm grip of the thumb on the outer shell 310, for example a rubber-like material, or may have a specific roughness (for example by creating a rough pattern in the mold) that may prevent the thumb from sliding off the outer shell 310 when opening the storage unit.

A connector 314 may be positioned substantially in the center of the container base 300, and according to one embodiment, may be used to connect container base 300 to a capsule holding unit 500. In some embodiments connector 314 may be positioned elsewhere, for example on the lid 600, or may be an integral part of container base 300 or liner 400. Other methods of connecting the base 300 to the holding unit 500 may be used, and in some embodiments the base and the holding unit may be integral, or the holding unit may be connected to a different portion, such as liner 400.

Figure 4:
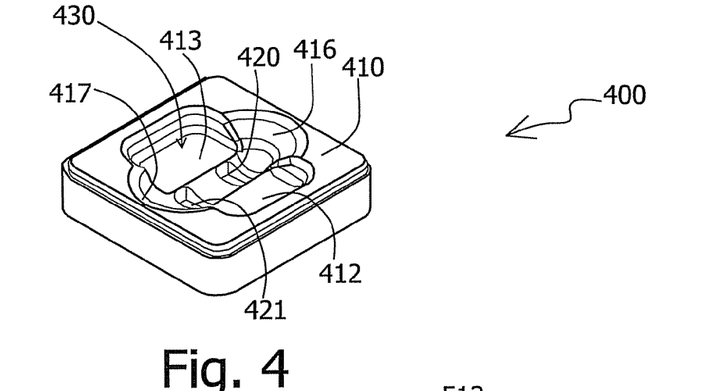
FIG. 4 is an exemplary configuration of a liner for a storage device according to an embodiment of the invention.

Reference is now made to FIG. 4, which is an exemplary configuration of a liner of a storage and activation unit according to an embodiment of the invention. In one embodiment, a liner 400 may be designed to be placed inside, or may be part of, a container base 300 of a device 200 for storing and activating an in vivo imaging capsule 40, such that the liner 400 is situated to fit, for example snugly or securely, inside the container base 300 substantially with no ability to move freely inside it (e.g., during shipping and handling of the imaging device's package). Preferably, the liner 400 may not move at all relative to the container base 300, for example in order to prevent breaking or damaging the imaging capsule 40 and/or in order to maintain the one or more optical domes 54, 54' substantially free of scratches and dents. The liner 400 may have a concave space 430, which may include one or more recessed sections 412, 413, 416 and 417. These sections, which may be recessed in relation to the top surface 410, may be substantially symmetrical, for example section 412 may be symmetrical to section 413, and/or section 416 may be symmetrical to section 417. The concave space 430 may be comprised of spherical recessed sections. In other embodiments the recessed sections need not be symmetrical and their shape, size, design and/or color may differ, for example according to the shape and size of the swallowable capsule 40 which the storage unit 200 holds, or according to an average size of a forefinger and thumb in different targeted patient groups (e.g., children vs. adults, etc.). Recessed sections 412 and/or 413 may be shaped to allow enough space for a user's fingers to firmly grasp the imaging capsule 40 which may be placed inside the recessed space. Preferably, the recessed sections 412 and 413 may be positioned such that the user's fingers may grab the capsule 40 substantially by touching the capsule housing 11, thereby maintaining the optical domes 54, 54' substantially free of fingerprints, sweat or dirt residue which may be rubbed off a user's fingers. Recessed sections 416 and/or 417 may be designed to fit the shape of the imaging capsule 40, for example to allow one or more optical domes 54, 54' of the imaging capsule 40 to lie inside the recessed sections 416 and/or 417 without touching any other component of the container 300, lid 600 or liner 400. The liner 400 may include one or more openings or fissures 420 and/or 421, which may allow, for example, one or more protruding sections such as 510, 511, 520 and/or 521 of a capsule holding unit 500 to fit into the fissures. Alternately, elements of capsule holding unit 500 may protrude from or be part of liner 400 itself, or may be part of container base 300 or lid 600. According to one embodiment, when the liner 400 is inserted into the container base 300, the flat upper surface 410 of liner 400 may be about the same level as the upper lip 316 of container base 300. In other embodiments, the upper surface 410 may be lower or higher than the upper lip 316. The depth of the indented spaces 412, 413, 416, 417 may be about the same depth as the container base 300 or may be less, such that the liner 400 will fit comfortably and easily into the container base 300. In some embodiments, depth of the indented spaces 412, 413, 416, 417 may differ from one section to another, or may be identical in each pair of symmetrical indented spaces.

In some embodiments, capsule 40 may be held entirely within the recessed space 430. In some embodiments, capsule 40 may be held partially above the level of surface 410 and partially below it. The recessed space 430 may be comprised of one or more recessed sections 412, 413, 416 and 417 or other recessed sections, which may be merged into a single recess or several separated recessed spaces in the unit 200.

Figure 5:
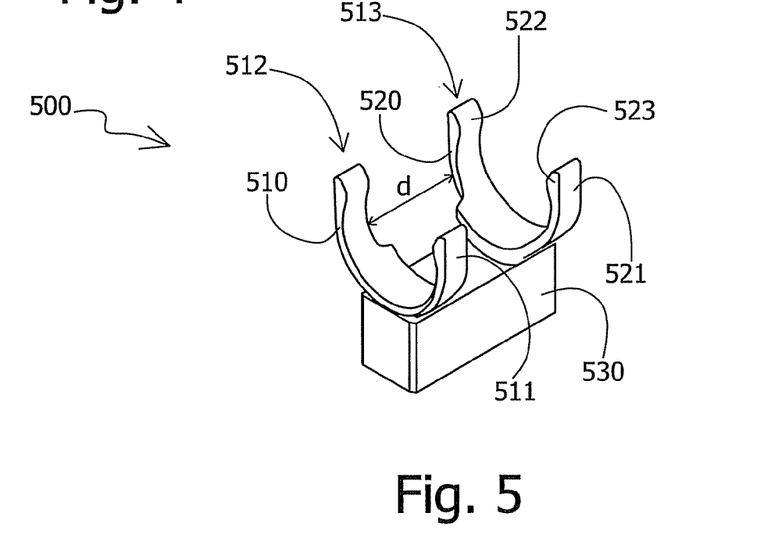
FIG. 5 is an exemplary configuration of a capsule holding unit according to an embodiment of the invention.

Reference is now made to FIG. 5, which is an exemplary configuration of a capsule holding unit 500 according to an embodiment of the invention. In some embodiments, the capsule holding unit 500 may be designed to fit inside or connect to a container base 300 or a liner 400. Capsule holding unit 500 may be shaped to hold or embrace a capsule 40, substantially around the capsule's circumference, for example around the capsule housing 11, along axis W shown in FIG. 1. According to one embodiment, the capsule holding unit 500 may include a base element 530, which may be shaped to fit or connect to a connector such as connector 314 for example, thereby connecting the capsule holding unit 500 and the container base 300. In other embodiments a separate connector need not be used, and in other embodiments holding unit 500 or its components may be connected to for example liner 400. On the base element 530 may be positioned two or more protruding elements 510 and 511 which construct a "C" shaped gripping unit 512. Each gripping unit 512 may include, for example, a set of two protruding elements 510 and 511 which may be held by the base element 530. One or more gripping units 512 and 513 may be used. Preferably, the capsule gripping unit(s) 512 and/or 513 may hold or contact the capsule 40 without touching or allowing any portion of the storing unit 200 to touch the capsule's optical dome(s) 54 and 54'. In some embodiments, capsule gripping unit(s) 512 and/or 513 contacts the housing 11 of capsule 40. In other embodiments, the capsule gripping unit(s) 512 and/or 513 may partially or completely touch a lower lip of the optical domes 54 and 54', for example the portion of the optical dome that is connected to the housing 11, in such a way that the capsule's field of view is not impaired, distorted or blocked. The gripping units 512 and 513 may have other shapes and sizes, for example according to the size and shape of the circumference of the capsule that they are designed to hold. The protruding elements 510 and 511 may be flexible, and may have spring back to their original position if they are pushed together or pulled apart. For example, if a capsule 40 is placed into the gripping units 512 and 513, the protruding elements 510 and 511 may be pulled back during insertion of the capsule 40 into position and once the capsule 40 is positioned in place (for example as shown in FIG. 2), the protruding elements 510 and 511 may spring back to their original position without the capsule, thereby holding the capsule 40 in the appropriate position in the storage unit 200. In one example, the protruding elements 510 and 511 may be positioned substantially symmetrically across from each other, for example on opposite sides of the recessed space 430. Other positions may be possible.

In some embodiments a capsule circumference may be, for example, an elongated oval, thus the gripping units 512, 513 may be substantially "U" shaped to fit the capsule. The capsule may be inserted into the capsule gripping unit(s) 512 and/or 513 for storing purposes, such that the capsule outer shell 11 and or domes are in contact with the gripping unit(s) 512 and/or 513. The protruding elements 510 and 511 and/or 520 and 521 may be made of a hard or semi-hard material such as acetal plastic and may be used to hold a capsule 40 in place by holding the capsule 40 for firmly but not overly tightly around its housing 11. In other embodiments, the protruding elements 510 and 511 and/or 520 and 521 may be made of a soft material or rubber-like material. Protruding elements 510 and 511 and/or 520 and 521 may hold the capsule's housing 11 or bottom part of the dome 54 and 54' without damaging (for example, without scratching it when the capsule 40 is removed from the gripping units 512 and 513). More than one holding unit 500 may be used. The tips of the one or more protruding elements 510 and 511 (for example teeth 522 and 523) may slightly protrude inward in order to better hold a capsule 40 in position. The capsule 40 may snap into a secure storing position in the gripping units 512 and 513 as a result of teeth 522 and 523. The gripping units 512 and 513 may be positioned to slide into slots or fissures 420 and 421. The distance d between gripping units 512 and 513 may be about a finger's width (for example about one centimeter apart), in order to enable easy removal of the capsule 40 from the storing unit 200 substantially by touching the capsule housing and without touching the optical domes 54 and 54'.

According to a different embodiment, a storage unit may be provided for holding a swallowable capsule with a single imaging head. For example, the capsule may be provided with an imaging head in one end, and a housing that covers the rest of it. In this embodiment, capsule holding unit 500 may include a capsule gripping unit 512, to hold the capsule near the imaging head. One or more positioning elements (not shown) may be provided, for example capsule gripping unit 513 may be replaced with a positioning element which may support or hold a non-imaging end of the capsule. The positioning element may be shaped for example as a half dome, in order to fit or partially cover the capsule end which may be placed into it. The positioning element may be made of a soft, rubber-like material, for example Santoprene™ material or similar materials which are soft or semi-soft, and thereby may preserve the capsule and position it securely without damaging it. The base element 530 may be shaped like an elongated box or a cube, or may have other shapes. On top of base element 530 may be assembled one or more capsule gripping unit(s) 512, and one or more positioning elements.

Figure 6A:
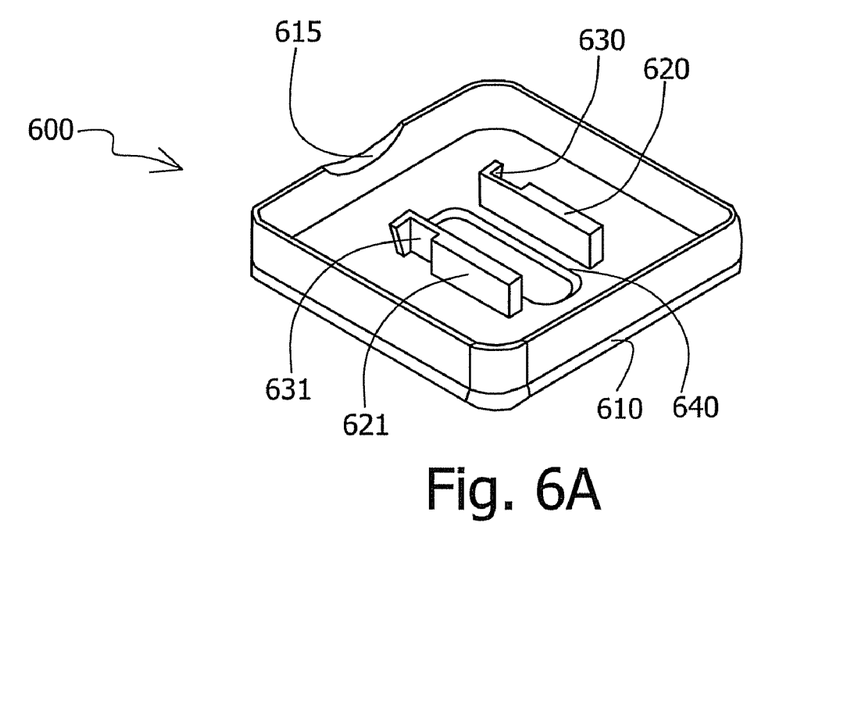
FIGS. 6A and 6B show a top view and a cross-sectional view of a lid of a storage device according to an embodiment of the invention.
Figure 6B:
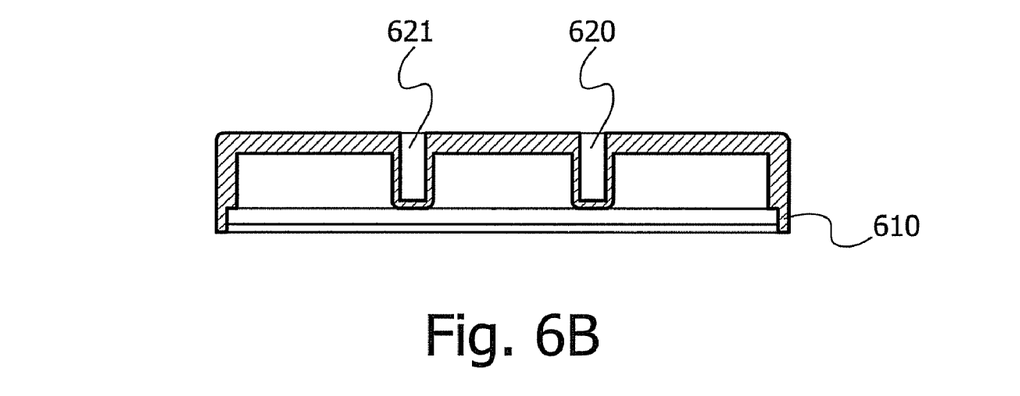

Reference is now made to FIGS. 6A and 6B, which show a top view and a cross-sectional view of a lid 600 of a storage device 200 for storing and activating an in vivo imaging capsule 40 according to an embodiment of the invention. In one embodiment, the lid 600 of the storage unit 200 may be made of a translucent or transparent material (such as polycarbonate), for example in order to see if the capsule 40 inside the device 200 is operating when the lid 600 is closed. In other embodiments, only part of the lid 600 may be transparent, for example only window 640 which may be shaped, for example, substantially like a capsule, a rectangle, an egg, a circle, etc. The lip 610 of the lid 600 may be indented, for example as shown in FIG. 6B, in order to fit tightly over the container base 300 when closing the lid 600.

Lid 600 may include one or more magnets 621 and/or 622, to activate and/or deactivate or otherwise control the capsule 40, for example while the capsule 40 is positioned inside storage unit 200. The magnets may be embedded into one or more fastening elements 630 and 631 which may be positioned on the lid 600, or may be connected to or part of another portion of the lid 600. The activation of the capsule 40 may occur when the lid 600 is opened. The capsule 40 may be removed from the storage unit 200 and may be placed back into the storage unit for deactivation. Placing the capsule 40 back for deactivation may in some embodiments require rotating the capsule 40 to a specific orientation in the storage device, for example along the axis L in FIG. 1, according to the orientation of the magnets placed in the storage unit 200 and magnetic switch 25 located in the capsule 40. Further, in a capsule with two imaging heads, if the first imaging head for example covered by dome 54 is placed near the side marked 416 in FIG. 4, the capsule 40 may be switched off or deactivated. In one embodiment, if the other imaging head, for example the one covered by dome 54' is placed near that same side, the capsule 40 may not be deactivated and may continue working until its position in the capsule holding unit 500 is changed (for example, by turning the capsule or changing the capsule's orientation along axis L and/or axis W in FIG. 1). In other embodiments a specific orientation of capsule 40 need not be required to activate or deactivate the capsule, rather the proximity of a magnet, or a movement, may cause activation. In other embodiments, the magnets 621 and/or 622 may be embedded into a different part of the storing unit 200, for example in the liner 400 or container base 300. In such embodiments, the activation of the capsule 40 may occur only when the capsule 40 is removed and distanced from the storing device 200, and not when the lid 600 is opened. If capsule 40 does not include a magnetic switch, but instead includes a different type of switch, for example an RF switch or a temperature switch, magnets 621 and/or 622 may not be required. Instead, lid 600 may include longer fastening elements which may press the protruding sections 510, 511 (and/or 520, 521) of one or more gripping units 512 and/or 513 towards each other (e.g., 510 may be pressed towards 511, and 520 may be pressed towards 521) and toward the inserted capsule 40 when lid 600 is closed. According to another embodiment, the magnets may press the protruding sections 510, 511 (and/or 520, 521) of one or more gripping units 512 and/or 513 towards each other. Other numbers of magnets or fastening elements may be used (e.g., one).

The magnets 621 and/or 622 may be positioned on the lid 600 such that when the lid 600 is closed, capsule 40 is deactivated, and when the lid 600 is open the capsule 40 is activated. In addition, when the lid 600 is closed, the magnets 621 and/or 622 and/or the fastening elements 630 and 631 may press protruding elements such as 510 and/or 511 inward (e.g., towards the inserted capsule 40), thereby holding and protecting capsule 40 securely in its position inside storage unit 200. When the lid 600 is opened, the pressure on the protruding elements 510, 511, 520, 521 of the capsule holding unit 500, which may be created by the magnets 621 and 622 and/or by fastening elements 630 and 631, may be reduced. Reducing the pressure on the protruding elements 510 and 511 and/or 520 and 521 may enable safe or easy removal of the capsule 40 from its casing without damaging the capsule 40 and without scratching its optical domes. When the lid 600 is closed, such additional pressure created by the fastening elements 630 and 631 or by the position of the magnets 620 and 621 on the lid 600 may enable safer shipping and handling of the capsule 40 in its package 200. In other embodiments, the magnets may be positioned elsewhere on the lid 600, or may be positioned in the capsule holding unit, for example in the capsule holding unit base element 530, in the container base 300, or in the liner 400. The pressure on one or more of the protruding elements 510, 511, 520, 521 when the lid is in closed position may be applied only by fastening elements such as 630 and 631. According to one embodiment, the lid 600 may also have an indented or concave portion 615, which may enable easier opening of the storage unit, for example in a similar manner to concave portion 312. Indented portion 615 may used for placing a finger or a thumb while opening and/or closing the storage device 200. The concave section 615 may be covered by a material that enables a firm grip of the thumb on the lid 600, for example a rubber-like material or may have a specific roughness (for example a different material could be used, or the same material as used for the lid 600 could be made coarse by creating a rough pattern in the mold) that may prevent the thumb from sliding off lid 600 when opening storage unit 200.

Figure 7A:
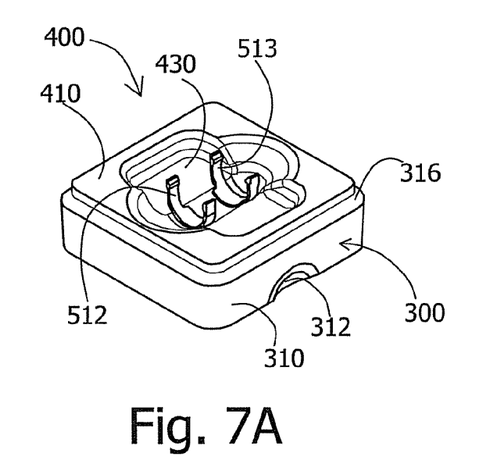
FIGS. 7A, 7B and 7C show an assembled storage device holding a capsule according to an embodiment of the invention.
Figure 7B:
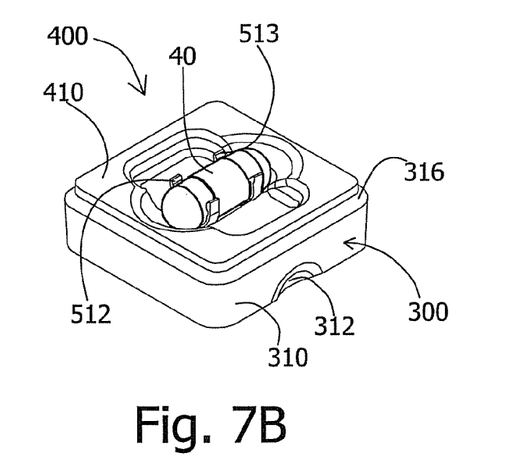
Figure 7C:
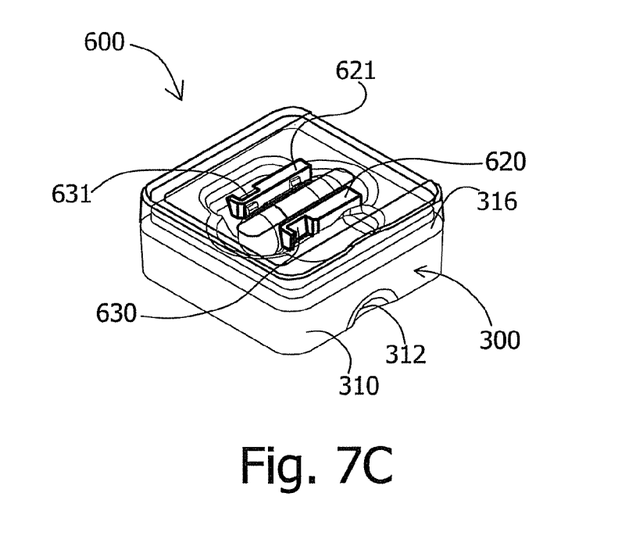

FIGS. 7A, 7B and 7C illustrate an assembled storage device for storing and activating an in vivo imaging capsule according to an embodiment of the present invention. In FIG. 7A, the container base 300 is shown, and fitted into it are the liner 400 and the capsule holding unit 500. The capsule holding unit 500 is connected to the liner 400 using the base of the holding unit (not shown), such that the gripping units 512 and 513 have their protruding elements 510, 511, 520 and 521 stick out above the recessed portion of liner 400. In FIG. 7B the capsule 40 is encased within the container base 300, the liner 400 and the capsule holding unit 500, and it is held in position by the two gripping units 512 and 513. In FIG. 7C, the capsule 40 is positioned inside the storage device 200, covered by lid 600, and two protruding elements 510, 511 are pressed tightly together by the magnets 620 and 621, and the other two protruding elements 520, 521 are pressed tightly together by the fastening elements 630 and 631.

Figure 8:
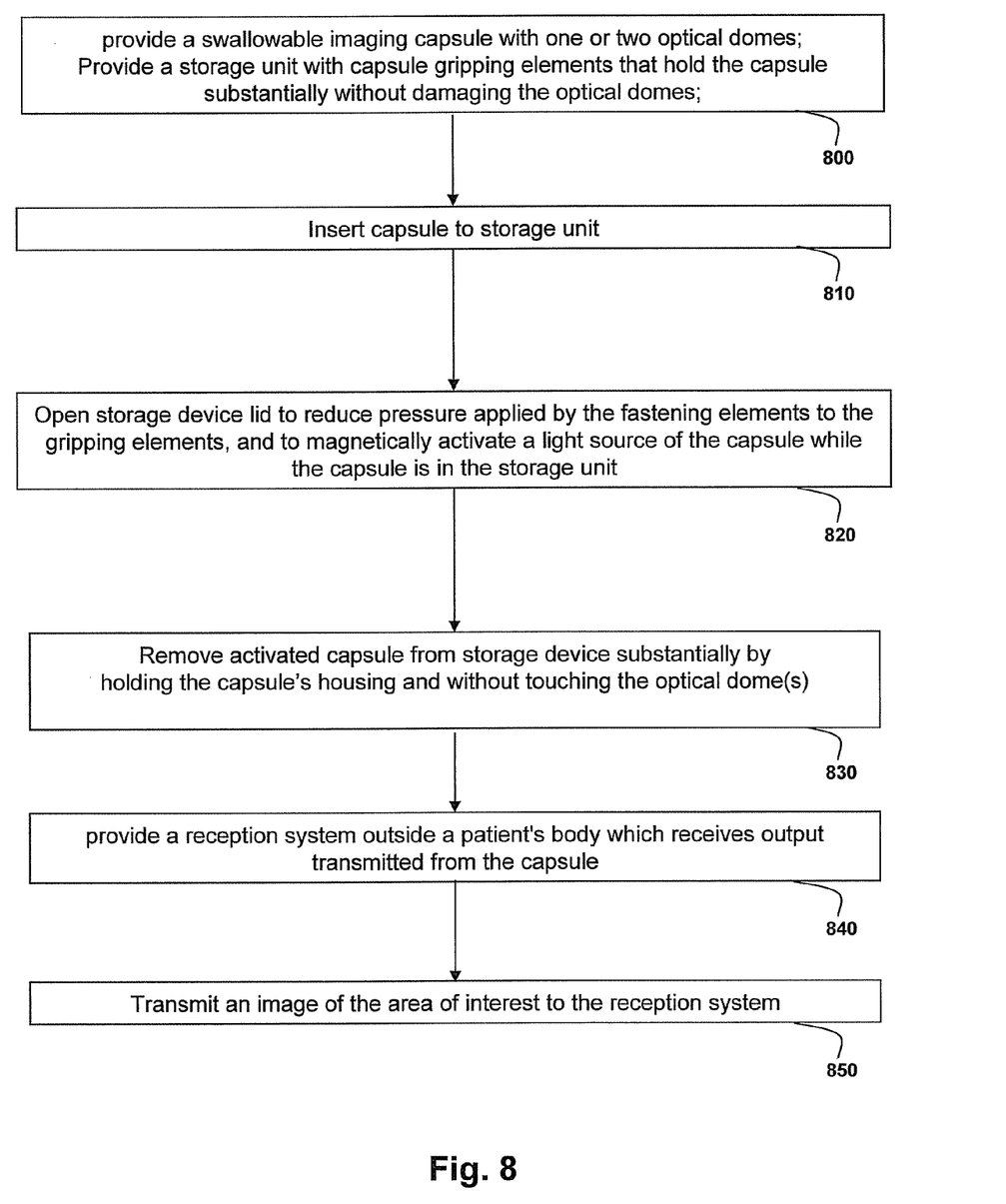
FIG. 8 is a flow chart of a method for storing and activating an in vivo imaging capsule according to an embodiment of the invention.

FIG. 8 illustrates a method of storing and activating a swallowable in vivo imaging capsule according to an embodiment of the invention. Step 800 may include providing a device such as swallowable imaging capsule 40 with one or two optical dome(s) 54 (and/or 54'), and providing a storage unit such as storage unit 200 with one or more capsule gripping elements 512 and/or 513, that may hold the capsule 40 substantially without damaging the optical domes 54 and 54'. Capsule 40 may be positioned in the storage unit 200 for example by capsule gripping elements 512 and/or 513 contacting the housing 11 of the capsule or a part of the optical dome which does not interfere with the imaging field of view of the capsule's one or more optical system(s). For example, if dome 54 continues below the level of the illumination sources 42 and 42', in some embodiments that portion of the dome may not be used for viewing the in vivo objects. In Step 810, capsule 40 may be inserted into the storage unit 200, for example during the process of packaging it for shipment in a production room. While in one embodiment, the devices and storage units described herein are used in an embodiment of the method, other embodiments of the method may use other devices and storage units.

Step 820 may include opening the lid 600 of the storage device, for example by a patient or a doctor before the capsule 40 is swallowed, or by a Quality Assurance professional who may check that capsule 40 is operating properly before it is shipped. Opening the lid 600 may reduce pressure applied to the gripping elements 512 and 513 by the fastening elements 630 and 631, and/or by the magnetic elements 620 and 621 which may also act as additional fastening elements in some embodiments. Opening the lid 600 may also magnetically activate an illumination source of the capsule 40, and may activate and initiate an image capturing mode of the capsule, for example while the capsule is still in the storage unit 200. In some embodiments, the image capturing mode may be activated only when the capsule 40 is removed from the storage unit 200 and distanced from it.

In Step 830 the activated capsule 40 may be removed from storage device 200, for example by a user, patient, doctor or production tester, by touching the capsule's housing 11 and without touching the optical dome(s) 54 and/or 54'. In Step 840 a reception system 12 may be provided outside a patient's body. The reception system may receive data transmitted from the capsule 40. In Step 850 capsule 40 may transmit in vivo images of an area of interest, for example the gastrointestinal tract, to the external reception system 12. In some embodiments, capsule 40 may flash or blink before being ingested (for example by intermittently switching on illumination sources 42 and 42'), and may thus provide to the doctor or patient a visual indication that it is activated and working. Capsule 40 may transmit images before being ingested, for example for verifying that all components of the capsule 40 (e.g. imagers, transmitters, antennas etc.) are working properly.

Figure 9:
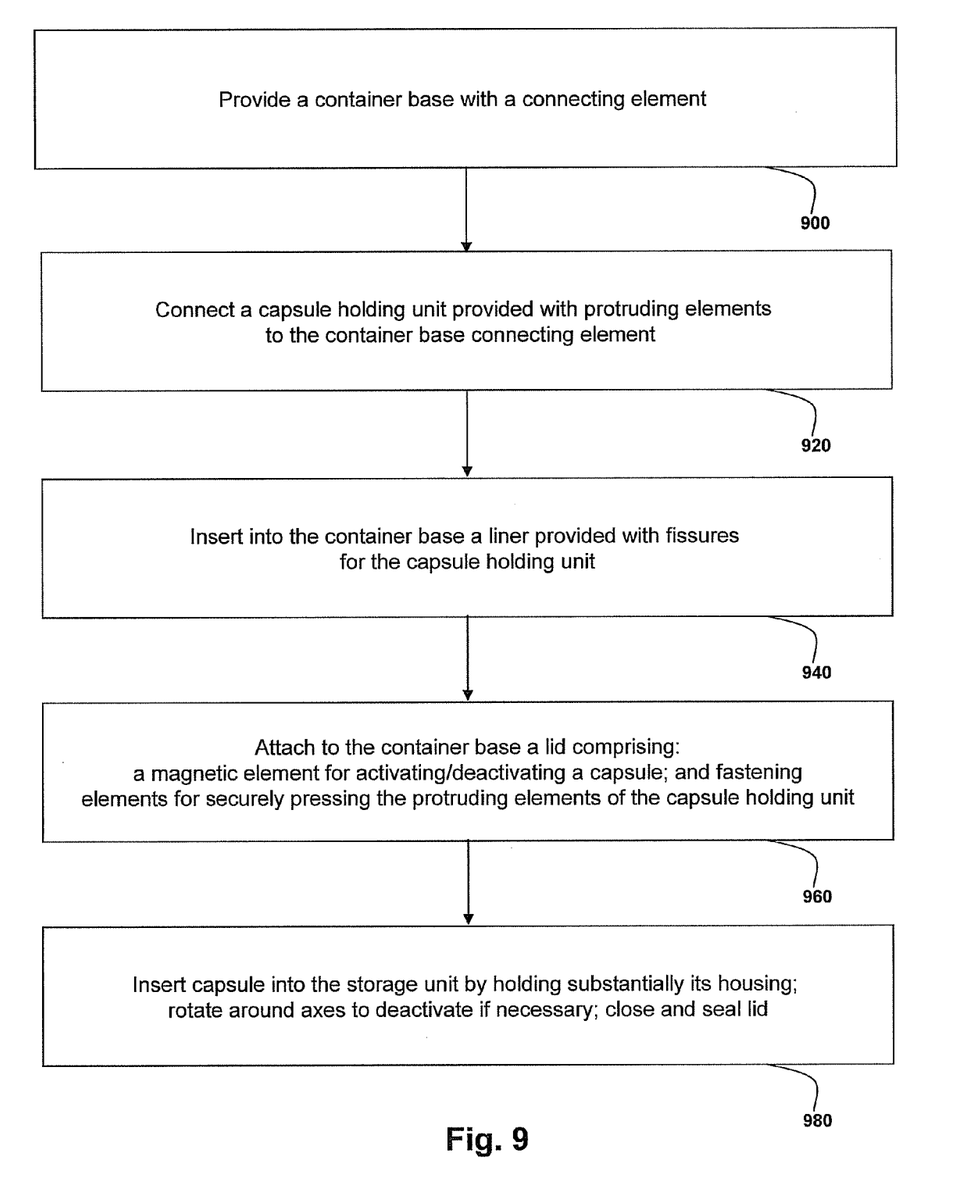
FIG. 9 is a flow chart according to embodiments of the present invention.

FIG. 9 is a schematic illustration of a method of manufacturing a storage and activation unit for a swallowable in vivo imaging capsule according to an embodiment of the invention. In step 900, a container base 300 may be provided, which may include a connector 314. In step 920, a capsule holding unit 500 may be provided with a base element 530 which may fit into the connector 314, and may also be provided with at least two protruding elements (such as 510, 511, 520 and 521), which make up one or more "C" shaped capsule gripping elements 512 and/or 513. The capsule holding unit 500 may be connected to the container base 300. In step 940, a liner 400 may be provided with one or more fissures 420 and/or 421. Liner 400 may include one or more positioning elements 550 that may support a capsule's end. Liner 400 may be assembled onto container base 300 or inserted into container base 300 such that the capsule gripping elements 512 and/or 513 may be inserted through the fissures, thereby connecting the liner 400 to the container base 300 and to the capsule holding unit 500 as shown in FIG. 7A.

In step 960 a lid 600 may be attached to the container base 300. The lid 600 may include one or more magnetic element(s) 620 and 621, for activating and/or deactivating the capsule. The lid 600 may also include fastening elements 630 and 631 for securely pressing the protruding elements 510, 511, and/or 520, 521 of the capsule holding unit 500, such that the protruding elements may be pressed inwards towards the capsule 40, thereby holding it in a secure position when lid 600 is closed. Lid 600 may be attached using various methods known in the art such as adhesive elements which act as pivot for opening and closing the lid, or screws, pins, etc.

In Step 980 capsule 40 may be inserted into the storage unit 200 by holding it by its housing 11, and lid 600 may be closed. It may be necessary to rotate the capsule around its longitudinal axis L to deactivate if it is operating after the lid is closed. It may also be necessary to change the orientation of the capsule 40, for example turn it 180 degrees around central axis W in order to position it correctly inside the storage unit 200 and thereby enable deactivation when the lid 600 is closed. After assuring that the capsule is deactivated, the lid may be sealed, for example hermetically to ensure sterility of the capsule.

It will be appreciated by persons skilled in the art that the present invention is not limited to what has been particularly shown and described hereinabove.

Having described preferred embodiments of the invention with reference to the accompanying drawings, it is to be understood that the invention is not limited to the precise embodiments shown and described hereinabove. Rather, various changes and modifications may be effected therein by those skilled in the art without departing from the scope or spirit of the invention, and the scope of the present invention is defined only by the claims, which follow.

What is claimed is:

1. A storage unit storing an in vivo imaging capsule, the in vivo imaging capsule being removable from the storage unit and having at least a housing and an optical dome, said storage unit comprising:
a recessed space accepting the in vivo imaging capsule, said recessed space comprising:
a recessed portion substantially in the shape of the in vivo imaging capsule; and
two recessed sections, each recessed section adjacent to the recessed portion and positioned to allow removal of the in vivo imaging capsule from the storage unit substantially by the action of the fingers of a user grabbing the housing of the in vivo imaging capsule without touching the optical dome;
a magnet for magnetically activating and deactivating the in vivo is imaging capsule; and
a capsule holding unit comprising at least two protruding elements to hold the in vivo imaging capsule in the storage unit until removal, said at least two protruding elements positioned to grip the housing of the in vivo imaging capsule and to allow removal of the in vivo imaging capsule from the storage unit by the action of the fingers of a user grabbing the housing of the in vivo imaging capsule without touching the optical dome; a lid comprising at least two fastening elements positioned such that when the lid is in a closed position, the at least two fastening elements press the at least two protruding elements inward towards the in vivo imaging capsule;
the in vivo imaging capsule holding unit being positioned substantially within the recessed space.

2. The device of claim 1, the magnet being positioned on the lid, such that the in vivo imaging capsule is activated when the lid is open, and the in vivo imaging capsule is deactivated when the lid is closed.

3. The device of claim 1, the magnet being embedded into the fastening element.

4. The device of claim 2, the lid having at least a portion made of a transparent material.

5. The device of claim 1, the protruding elements being positioned substantially symmetrically across from each other on opposite sides of the recessed space.

6. The device of claim 1, the holding unit comprising two capsule gripping units, each capsule gripping unit comprising two protruding elements positioned substantially symmetrically across from each other on opposite sides of the recessed space.

7. The device of claim 6, the capsule gripping units being positioned substantially one centimeter apart from each other.

8. A storage device for storing a swallowable capsule, the swallowable capsule comprising a housing and an optical dome, the storage device comprising:
a container base comprising a recessed space for placing the swallowable capsule;
a capsule holding unit positioned substantially within the container base, the capsule holding unit comprising at least two protruding elements positioned to removably hold the swallowable capsule around its housing, the protruding elements being positioned across from each other on opposite sides of the recessed space; and
a lid for covering the container base, the lid comprising a magnet, wherein the magnet is positioned to activate the swallowable capsule when the lid is open, and to deactivate the swallowable capsule when the lid is closed, and the lid comprising at least two fastening elements to apply pressure to the at least two protruding elements, such that when the lid is closed the at least two fastening elements press the at least two protruding elements inward, towards the swallowable capsule, thereby providing an additional pressure for holding the swallowable capsule in the capsule holding unit.

9. The device of claim 8, further comprising a liner assembled into the container base.

10. The device of claim 8, the magnet being embedded into one of the at least two fastening elements.

11. The device of claim 8, wherein at least a portion of the lid is made of a transparent material.

12. The device of claim 8, the protruding elements being positioned substantially symmetrically across from each other.

13. An apparatus for storing and activating a swallowable in vivo device comprising a dome a housing, the apparatus comprising:
   a container base comprising a recessed space, the recessed space formed to accept the swallowable in vivo device and comprising:
      a recessed portion substantially in the shape of the swallowable in vivo device; and
      two or more recessed sections, adjacent to the recessed portion, positioned to allow removal of the swallowable in vivo device from the storage unit by the action of the fingers of a user grabbing the housing of the swallowable in vivo device without touching the optical dome;
   a device holding unit comprising at least two protruding elements to removably hold the swallowable in vivo device in the apparatus, said at least two protruding elements positioned to grip the housing of the swallowable in vivo device and to allow removal of the swallowable in vivo device from the storage unit by the action of the fingers of a user grabbing the housing of the swallowable in vivo device without touching the dome;
   a lid for covering the container base, the lid being attached to said container base by a pivot member acting as a reusable pivot for opening and closing the lid, the lid comprising at least two fastening elements to apply pressure to the at least two protruding elements, such that when the lid is closed the at least two fastening elements press the at least two protruding elements inward, towards the swallowable in vivo device, thereby providing an additional pressure for holding the swallowable in vivo device in the device holding unit; and
   a magnet positioned in the lid to activate the swallowable in vivo device when the lid is open and deactivate the swallowable in vivo device when the lid is closed.

14. The apparatus of claim 13, said magnet being curved so that no specific orientation of the swallowable in vivo device is required to activate or de-activate the swallowable in vivo device.

15. The apparatus of claim 13, said device holding unit comprising a positioning element shaped to hold an end of the swallowable in vivo device.

16. The apparatus of claim 15, said dome of the swallowable in vivo device being positioned at a first end of the housing and said swallowable in vivo device further comprising a non-domed end positioned at a second end of said housing, said positioning element holding the non-domed end of the swallowable in vivo device.

17. The apparatus of claim 15, said positioning element shaped as a half-dome.

18. The apparatus of claim 15, said positioning element shaped to cover the end of the swallowable in vivo device being held.

* * * * *